(12) United States Patent
Brasch et al.

(10) Patent No.: US 9,940,807 B1
(45) Date of Patent: Apr. 10, 2018

(54) SYSTEM AND METHOD FOR MONITORING MULTIPLE PATIENTS

(71) Applicant: J. Brasch Co., LLC, Lincoln, NE (US)

(72) Inventors: John Joseph Brasch, Lincoln, NE (US); Gordon Smith, Jr., Lincoln, NE (US); James Leacock, Lincoln, NE (US)

(73) Assignee: J. Brasch Co., LLC, Lincoln, NE (US)

( * ) Notice: Subject to any disclaimer, the term of this patent is extended or adjusted under 35 U.S.C. 154(b) by 0 days.

(21) Appl. No.: 14/474,894

(22) Filed: Sep. 2, 2014

Related U.S. Application Data

(60) Provisional application No. 61/872,739, filed on Sep. 1, 2013.

(51) Int. Cl.
| | | |
|---|---|---|
| *G08B 1/00* | (2006.01) | |
| *G08B 21/02* | (2006.01) | |
| *G08B 21/18* | (2006.01) | |
| *A61B 5/00* | (2006.01) | |
| *A61B 5/11* | (2006.01) | |

(52) U.S. Cl.
CPC ............ *G08B 21/02* (2013.01); *A61B 5/0002* (2013.01); *A61B 5/1113* (2013.01); *G08B 21/18* (2013.01)

(58) Field of Classification Search
CPC ... G06F 19/3418; G06F 19/34; A61B 5/0022; A61B 5/0002; G08B 21/0211
See application file for complete search history.

(56) References Cited

U.S. PATENT DOCUMENTS

| | | | | |
|---|---|---|---|---|
| 6,406,426 B1 * | 6/2002 | Reuss | ................. | A61M 5/1723 128/903 |
| 2005/0188263 A1 * | 8/2005 | Gross | ................. | G06F 11/0751 714/25 |
| 2005/0242946 A1 * | 11/2005 | Hubbard, Jr. | ........ | G06F 19/3418 340/539.12 |
| 2007/0011389 A1 * | 1/2007 | Nishikawa | ............ | G06F 13/362 710/309 |
| 2008/0025330 A1 * | 1/2008 | Wang | ................. | H04L 63/0428 370/406 |
| 2010/0076782 A1 * | 3/2010 | Denholm | .............. | G06F 3/0219 705/2 |
| 2010/0265073 A1 * | 10/2010 | Harper | ................. | A61B 5/0031 340/573.1 |
| 2011/0218418 A1 * | 9/2011 | Green | ................. | A61B 5/0002 600/386 |
| 2011/0277242 A1 * | 11/2011 | Dionne | ................. | A61G 7/005 5/611 |
| 2013/0096953 A1 * | 4/2013 | Beverly | .............. | G06F 19/3418 705/3 |
| 2013/0159561 A1 * | 6/2013 | Cong | ................. | G06F 11/3034 710/19 |

* cited by examiner

*Primary Examiner* — Hongmin Fan
(74) *Attorney, Agent, or Firm* — Michael D. Eisenberg

(57) ABSTRACT

A system for monitoring multiple patients within a facility comprises a plurality of monitoring apparatuses, a central communication hub, and a plurality of notification devices. The monitoring apparatuses generate data relating to the status of patients, and send the data to the communication hub. The data may include an alarm signal. In a variant, the monitoring apparatuses do not generate alarm signals. Rather the communication hub processes the data and generates alarms if needed. Alarms are sent by the communication hub to the notification devices to inform employees of the facility of the source of the alarm.

24 Claims, 7 Drawing Sheets

SYSTEM AND METHOD FOR MONITORING MULTIPLE PATIENTS

CROSS-REFERENCES TO RELATED APPLICATIONS

The present application claims priority from U.S. Provisional Application Ser. No. 61/872,739 filed on Sep. 1, 2014, which is hereby incorporated herein by reference in its entirety.

TECHNICAL FIELD

The present invention, in some embodiments thereof, relates to medical devices, and more particularly to medical devices and systems for monitoring elderly patients.

BACKGROUND OF THE INVENTION

Alarm fatigue occurs when one is exposed to a large volume of alarms and as a result, one can become desensitized to the firing alarms. Desensitization can lead to longer response times or missing important alarms. Alarm fatigue occurs in many industries including construction, mining, and healthcare.

The constant sounds of alarms and noises from blood pressure machines, ventilators and heart monitors causes a "tuning out" of the sounds due to the brain adjusting to stimulation. This issue is present in hospitals, in home care providers, nursing homes and other medical facilities alike. The Joint Commission's sentinel event reports 80 alarm-related deaths and 13 alarm-related serious injuries over the course of a few years. On Apr. 18, 2013, the Joint Commission issued a sentinel event alert that highlighted the widespread problem of alarm fatigue in hospitals. The Joint Commission recommended establishing guidelines to tailor alarm settings, training all members of the clinical team on safe use of alarms, and sharing information about alarm-related incidents. This alert has since turned into a National Patient Safety Goal for 2014 to improve the safety of clinical alarm systems. This Goal will force hospitals to establish alarm safety as a priority, identify the most important alarms, and establish policies to manage alarms by January 2016.

Hospitals across the country are looking for ways to reduce the threat. Alarms that are more critical, i.e. heart rate, oxygenation, are usually louder, sound at a higher pitch, and sound more rapidly. Less critical alarms may sound at a lower and slower pitch. Other hospitals have a centralized monitoring station where an individual or individuals are only responsible for monitoring critical heart rate monitors.

ECRI (Emergency Care Research Institute), a not-for-profit organization dedicated to patient safety, outlines the following strategies for managing alarm fatigue. They suggested strategies like using a multidisciplinary team to review the issues, review events and near misses, take time to observe how alarms are responded to, ask nurses and other healthcare providers about their concerns, identify vulnerabilities and implement both short and long term fixes to the problem.

Strategies related to ECG monitoring include improving skin prep to reduce lead failure, routinely change electrodes, replace batteries regularly and to raise the priorities of the alarms relating to the disconnection of leads from the patient's body. Other considerations include delineating who is responsible for what alarms, identify back up coverage and response.

Brief Summary of Embodiments of the Invention

Instead of lessening the effects of alarm fatigue via training, guidelines, or differentiated alarms, the present invention aims at reducing the source of alarm fatigue, i.e. reducing noise from alarms in medical facilities, assisted living communities, and continuing care retirement communities.

In some embodiments of the present invention, a system is provided, which includes a plurality of monitoring apparatuses, a central communication hub, and a plurality of notification devices, which are optionally configured for being carried by employees of the facility. The monitoring apparatuses generate data relating to the status of patients, and send the data to the communication hub. The data may include an alarm signal. In a variant, the monitoring apparatuses do not generate alarm signals. Rather the communication hub processes the data and generates alarms if needed. Alarms are sent by the communication hub to the notification devices. In this manner, the closest employee can reach the patient in need and turn off the alarm, reducing the time interval in which the alarm is active. Moreover, in the embodiments in which the notification devices are carried by the employees, the need for speakers which loudly emit alarm sounds is obviated. In fact, softer alarms sounds may be emitted by the notification devices. Therefore, by enabling shorter and softer alarms, the present invention can reduce alarm fatigue.

An aspect of some embodiments of the present invention relates to a system for monitoring multiple patients within a facility. The system includes a plurality of monitoring apparatuses, a central communication hub, and a plurality of notification devices. Each monitoring apparatus corresponds to at least one respective patient, and is configured to be in communication with a respective sensing unit which comprises at least one sensor configured for creating sensing data indicative of a status of the patient. Each monitoring apparatus comprises a respective control unit and a respective communication unit. The control unit is configured for being in wired and/or wireless communication with the sensing unit, and for receiving the sensing data. The communication unit is configured for receiving the sensing data from the control unit and transmitting the sensing data to a remote location. The central communication hub is configured for being in communication with the plurality of monitoring apparatuses, and for receiving the sensing data from each communication unit. The central communication hub and/or the control unit is configured for processing the sensing data, and generating an alarm signal if at least a portion of the sensing data deviates from a predetermined pattern, the deviation being indicative of an undesirability in the patient's status. The plurality of notification devices are configured for being in wired and/or wireless communication with the central communication hub, each notification device being configured for being accessible to one or more employees of the facility, and each notification device comprising a communication element configured for receiving the alarm signal and an output element informing the one or more employees about the source of the alarm signal.

In a variant, the patient's status comprises at least one of: the patient's presence in at least one particular location, absence from at least one particular location, a position of the patient, a stance of the patient.

In another variant, the central hub is associated with a memory utility configured for storing the sensing data and/or the alarm signal corresponding to each monitoring apparatus.

Optionally, the central hub is configured for monitoring an amount of free memory in the memory utility, and for generating and sending a notification to at least one of the notification devices when the amount of free memory is less than a predetermined amount.

Optionally, at least one of the notification devices is configured for storing the sensing data and/or the alarm signal when the amount of free memory in the memory utility is less than a predetermined amount.

In yet another variant, each monitoring apparatus comprises at least one output unit configured for delivering a message to the respective patient, when the alarm is generated.

Optionally, the output unit is associated with a memory unit storing a plurality of messages corresponding to a plurality of causes due to which the alarm has been generated, the output unit being configured for selecting one of the messages, depending on the cause for due to which the alarm has been generated.

Optionally, the central communication hub is configured for generating data indicative of the message in response to the alarm signal, and for transmitting the data indicative of the message to the monitoring apparatus. The output unit is configured for delivering the message based on the data indicative of the message.

In a further variant, at least one of the monitoring apparatuses comprises at least one output unit. At least one of the notification devices comprises at least one input unit configured for receiving a message input from the one or more employees, the message input being indicative of a message to the patient. The communication hub is configured for delivering the message input to the at least one monitoring apparatus. The at least one output unit is configured for delivering a message to the corresponding patient, the message being based on the message input.

Optionally, the message input comprises at least one of: a press of a button of the notification device, a tap of a button of the notification device, a touch of a touchscreen of the notification device, a swipe of the touchscreen of the notification device.

In yet a further variant, each of at least some of the communication units comprise respective user interfaces configured for enabling the one or more employees to respond to the alarm, the response causing the respective devices to generate instruction data and send the instruction data to the central communication hub, the instruction data causing the central communication hub to communicate with all other notification devices in use so as to inform other employees that the alarm has been responded to.

In a variant, the notification device is configured for emitting a low-volume warning sound in response to receiving the alarm signal.

In another variant, the notification device comprises a display configured for displaying an image indicative of the source of the alarm signal in response to the notification device's receipt of the alarm signal.

Optionally, the image comprises a map of the facility and a mark on the map displaying a location of the source of the alarm.

In yet another variant, the notification device is configured for generating haptic feedback in response to receiving the alarm signal.

In a further variant, at least one control unit is connected to a plurality of sensing units associated with a plurality of respective patients.

In yet a further variant, the control unit is configured for being in communication with at least one sensing unit which comprises a plurality of sensors.

Optionally, each sensor is connected to the control unit and is configured for communicating with the control unit by wire and/or wirelessly.

In some embodiments of the present invention, the monitoring apparatuses are disposed in series with each other in a partial mesh network configuration, such that any given monitoring apparatus is configured for receiving first sensing data and/or a first alarm signal from a preceding monitoring apparatus and for conveying the first sensing data and/or the first alarm signal to a following monitoring apparatus along with the sensing data and/or the alarm signal generated by the given monitoring apparatus. A last monitoring apparatus of the series is configured to be in direct communication with the central communication hub and for conveying to the central communication hub the sensing data and/or alarm signals of all other monitoring apparatus along with the sensing data and/or the alarm signal generated by the last monitoring apparatus.

Optionally, the monitoring apparatuses comprise a first set of monitoring apparatuses and a second set of monitoring apparatuses. In the first set, the monitoring apparatuses are disposed in a first series, such that a last monitoring apparatus of the first series is configured to be in direct communication with the central communication hub. In the second set, the monitoring apparatuses are disposed in a second series, such that a last monitoring apparatus of the second series is configured to be in direct communication with the central communication hub.

Optionally, any particular monitoring apparatus of the first set is configured to be in communication with a previous communication apparatus, a following apparatus in the first set, and at least one monitoring apparatus of the second set. Any monitoring apparatus of the first set is configured for conveying the received and generated sensing data and/or alarm signal to the following monitoring apparatus of the first set. If the following monitoring apparatus in the first set is not responsive to communication, the monitoring apparatus of the first set is configured to convey the received and generated sensing data and/or alarm signal to the at least one monitoring apparatus of the second set. Any particular monitoring apparatus of the second series is configures to be in communication with a previous monitoring apparatus, a following monitoring apparatus in the second set, and at least one monitoring apparatus of the first set. Any monitoring apparatus of the second set is configured for conveying the received and generated sensing data and/or alarm signal to the following monitoring apparatus of the second set. If the following monitoring apparatus in the second set is not responsive to communication, the monitoring apparatus of the second set is configured to convey the received and generated sensing data and/or alarm signal to the at least one monitoring apparatus of the first set.

In a variant, the central communication hub is associated with a server, and at least one of the monitoring apparatuses is configured for being programmable via the server and/or via a computing device in communication with the server.

In another variant, the central communication hub is associated with a server. The central communication hub is configured for using the sensing data corresponding to at least one of the patients for generating a report relating to the at least one of the patients. The report is accessible via the server and/or via a computing device in communication with the server.

In yet another variant, each notification device is configured for being carried by a respective employee.

In a further variant, at least one of the monitoring apparatuses comprises a respective sensing unit.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
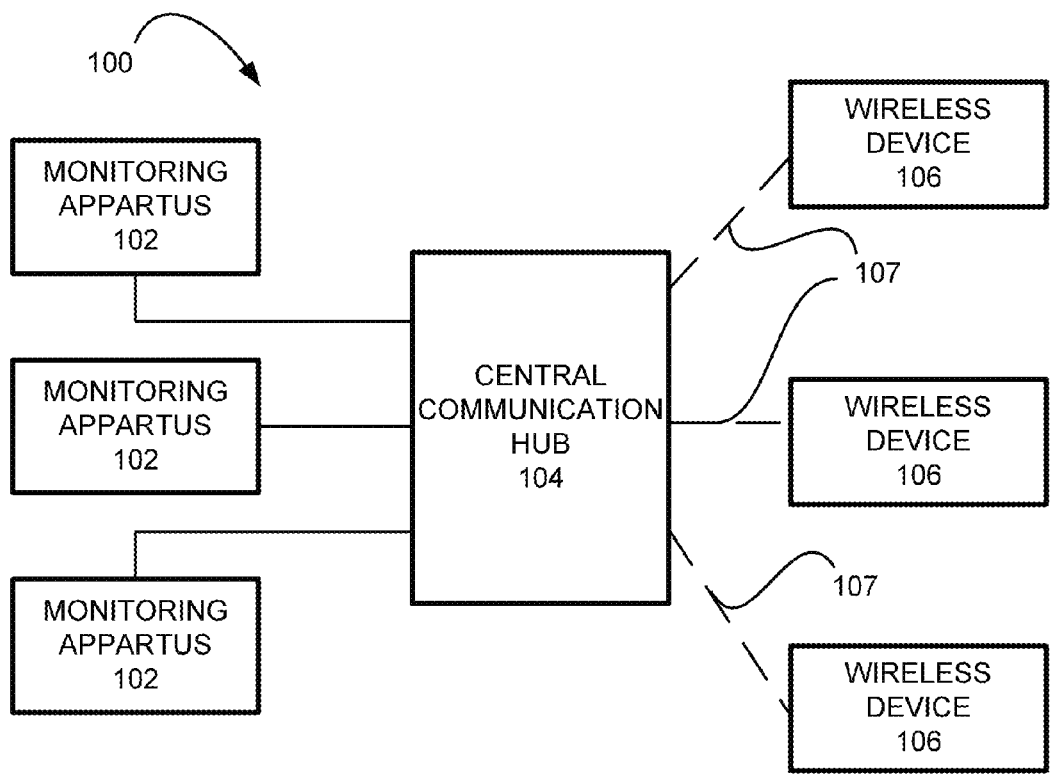
FIG. 1 is a box diagram illustrating the system of the present invention.

FIG. 1 is a box diagram illustrating the system of the present invention. The present invention is configured for being used in facilities in which the residents or patients are in need of medical monitoring, such as hospitals, assisted living communities, continuing care retirement communities, and old age homes. In the following, a monitored person will be called a patient, but may also be a resident.

The system 100 comprises a plurality of individual patient monitoring systems 102, a central communication hub 104 and a plurality of notification devices 106. Each of the monitoring apparatuses is configured for being associated with one or more sensors which are configured for generating sensing data indicative of the status of a patient. The monitoring apparatuses are configured for receiving the sensing data from the one or more sensors. Each monitoring apparatus is connected by wire or wirelessly to the central communication hub 104. The connection between the monitoring apparatuses and the central communication hub 104 may be direct or via a network.

The central communication hub 104 communicates with the notification devices via a wired or wireless signal 107, and conveys an alarm signal indicative of an undesirable status of at least one of the patient to the notification devices. The alarm signal may be generated by the monitoring apparatuses and/or by the central hub based on the sensing data. In a variant, the notification devices are configured for being carried by employees of the facility, such as doctors, nurses, etc. In another variant, the notification devices are configured for being installed in the facility, for example in a nurse's station, or mounted on the walls of the facility]. The alarm signal received by the notification devices causes the notification devices to emit an alarm (e.g., by sound, vibration, light, and/or image) in order to inform the employees about the source of the alarm. In this manner, the employees of the facility are able to locate the source of the alarm and help the patient in need.

Figure 2:
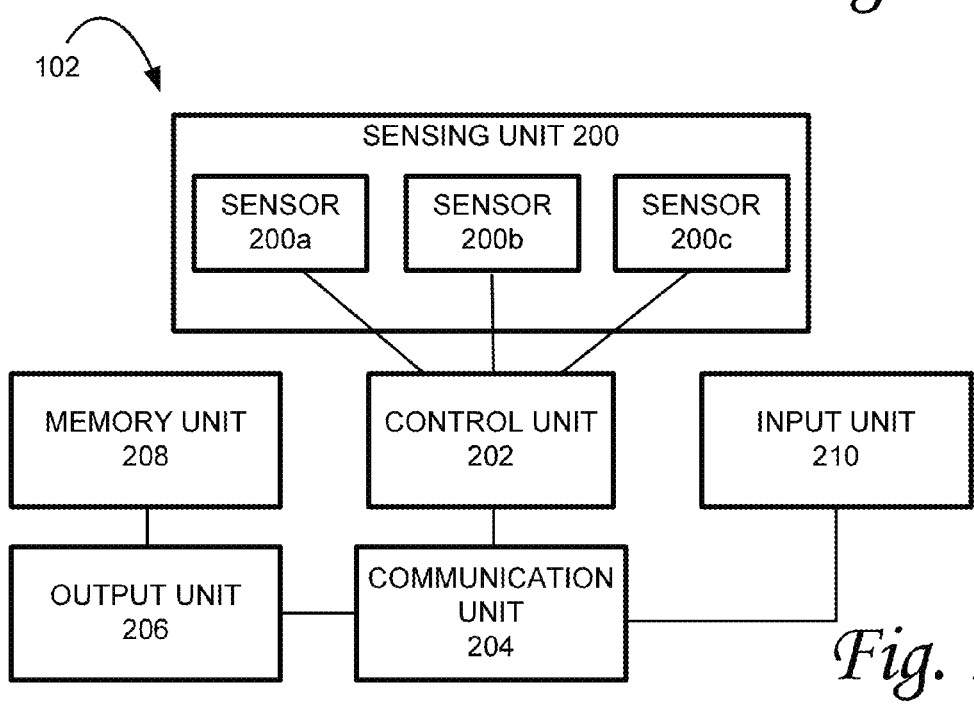
FIG. 2 is a box diagram illustrating a monitoring apparatus, according to some embodiments of the present invention.

FIG. 2 is a box diagram illustrating a monitoring apparatus, according to some embodiments of the present invention The monitoring apparatus 102 is associated with a sensor unit 200, a control unit 202, and a communication unit 204. The sensor unit 200 may or may not be included in the monitoring apparatus. The sensor unit includes one or more sensors (200a, 200b, 200c) configured for sensing one or more parameters that relate to the patient's status. The sensors may include a pressure and/or heat sensor placed under a bed or chair to monitor a patient's position and/or movement in a bed or chair. Additionally or alternatively, the sensors may include an infrared sensor in the vicinity of the patient's room door, to detect whether the door is open or closed (so as to determine whether the patient has left the room or a nurse has entered the room). Additionally or alternatively, the sensors may include a blood pressure sensor and/or, heart rate sensor, and/or any other biometric sensor. Additionally or alternatively, the sensors may include motion detectors, cameras, and/or microphones.

The sensors generate sensing data and transmit the sensing data to the control unit 204. The control unit 204 is configured for receiving the sensing data and formatting the data for transmission to a remote location.

Optionally, the control unit is configured for processing the sensing data and generating an alarm signal if at least a portion of the sensing data deviates from a predetermined pattern. For example, if pressure or heat on a patient's bed are below a predetermined threshold during the patient's usual bed time, the patient may be absent from the bed. This may indicate that the patient may have fallen. In another example, if the infrared sensor indicates that the door of the patient's room has been opened during the patient's bedtime, the patient may have left the room. This would be undesirable for a patient with Alzheimer's disease whose behavior is unpredictable, or may be indicative of the entry of a stranger in the room. In yet another example, if the biometric sensor detects a parameter (blood pressure, heart rate, body temperature, etc.) outside a predetermined range, the patient's be going through an undesirable condition, such as hostility, shock, heart failure, high fever, etc., and may be in need of assistance. In a further example, a microphones placed within a patient's room may be configured to detect changes in sound. The lack of sound can indicate that a patient has not been moving in the room for an extended period of time and may need to have a nurse or other caregiver to check his vital signs. A sudden and loud noise may indicate a fall and the need for immediate assistance.

The communication unit 204 is configured for communicating with the central communication hub, and for sending the sensing data and/or the alarm signal to the communication hub. Optionally, the communication unit 204 is configured for receiving a communication/data/instruction from the communication hub 104.

Optionally, the monitoring apparatus 102 includes an output unit 206, configured for conveying a message to a patient in need of assistance, in order to help calm the patient until the arrival of medical personnel. The message may include a calming message and/or instructions to perform one or more actions. The output unit may include a speaker, and/or a display, and/or a light. The output unit is configured for conveying the message if an alarm signal has been generated by the control unit 202. The calming message may be in the form of an audio message, and/or a still image, and/or a movie. Optionally, the monitoring apparatus 102 includes a memory unit 208 storing the calming message.

Optionally, the memory unit 208 stores a plurality of calming messages, each message being appropriate for a different ailment or distress the patient may be experiencing. Alternatively or additionally, the central communication hub 104 is configured for dynamically generating the message in response to the sensing data conveyed thereto by the monitoring apparatus 102, and for communicating the message to the monitoring apparatus 102, which in turns convey the message to the patient. The message may be individualized for the patient. For example, the message may include the voice, photograph, movie of a person known to the patient. In some embodiments of the present invention, the communication unit 204 is configured for receiving a voice (audio) message from an employee of the facility, and the output unit includes a speaker which emits the employee's voice.

Optionally, the monitoring apparatus 102 includes an input unit 210, such as a microphone and/or a camera, configured for receiving a voice or image input from the patient. The input is transmitted to the central hub by the communication unit 204, and may enable employees of the facility to have a better understanding of the patient's status before reaching the patient's room. The input unit 210 and the output unit 206 may enable a direct voice-to-voice communication between the patient and an employee of the facility.

In some embodiments of the present invention, the sensing unit is configured to sense the position of a patient while in a bed. For example, the sensing unit may include smaller individual sensors placed in the center and along the outer edges of the pad. If a patient is positioned normally in bed, the only active sensor is the center one. If the patient starts to get out of bed, as he/she rolls out, one of the outer sensors in activated providing a warning to the caregiver. An example of such a sensing unit is described in U.S. Pat. No. 5,844,488, which is included by reference in this document.

The memory utility 208 may be configured for storing sensing data for later use.

It should be noted that a monitoring unit may be used for monitoring one patient or a plurality of patients inside a room. For example, in a room with two patients, two sets of sensors may communicate with the control unit. The first set of sensors is configured for sensing parameters relating to the status of the first patient and the second set of sensors is configured for sensing parameters relating to the status of the second patient.

Figure 3:
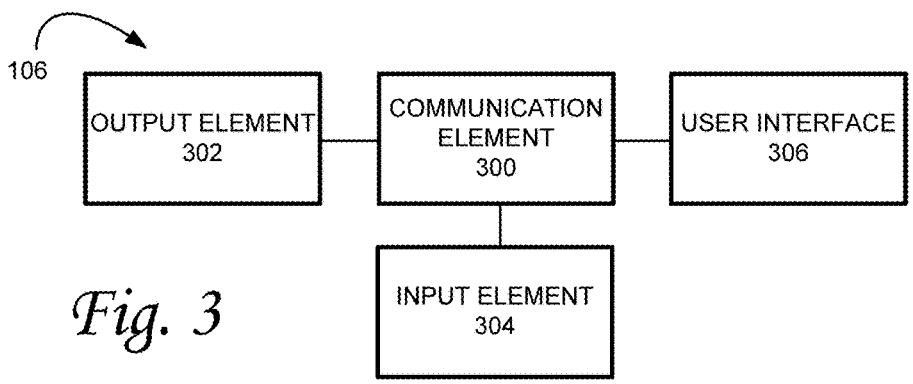
FIG. 3 is a box diagram illustrating a notification device, according to some embodiments of the present invention.

FIG. 3 is a box diagram illustrating a notification device 106, according to some embodiments of the present invention. The notification device 106 includes a communication element 300 and an output element 302. The communication element is configured for receiving the alarm signal and/or sensing data from the central communication hub. The output element 302 is configured for informing the employee about an alarm, the source of the alarm, and optionally about the condition of the patient. The output element may include a speaker configured for emitting an alarm sound, and a display configured for displaying information regarding the source and/or the cause of the alarm. In the embodiment in which the output element includes a speaker, the output element may be configured for emitting sounds of varying decibel levels and different types of tones. The output element may include a haptic feedback element, such as a vibrating element, which vibrates in response to the alarm signal. The above notification mechanisms are described by way of example. The scope of the present invention extends to any kind of output element configured for notifying the employee about the alarm in any manner.

Optionally, the output element includes a display configured for displaying a map of the facility and for indicating with a mark the location from which the alarm originated. In some embodiments of the present invention, the map of the premises has color indicators on each room so that employees can determine information relating of the patients, the information being based on data from one, some or all of the sensors in the patients room, The information extracted by the sensing data may indicated, for example, who is in bed and who is out of bed, whether the doors of the patients' rooms are open, whether patients' biometric measurements are within specific ranges, etc. Additionally, the map may have icons for the bed, chair, and doors for each patient's room that flash and/or change colors when there is a change in the patient's room. In one non-limiting example, the color change may be based on the time since a patient was check on and/or on the time since the generation of the alarm signal. In this manner, alarms which have been activated for an extended time can be prioritized. In another non-limiting example, colors correspond to certain parameters indicative of the wellbeing of the patients. Thus, colors may change and/or flash when the wellbeing of the patients change.

Optionally, the notification device 106 includes an input element 304, such as a microphone and/or camera, configured for receiving a speech and/or image of the employee. The speech and/or image is converted to audio data and/or visual data, which is transmitted via the communication element 300 to the communication hub and to the monitoring unit in the patient's room. In this manner, the employee may be able to convey a message to the patient before arriving to the patient's room. As explained above, the message may originate from the hub or the monitoring apparatus. In some embodiments of the present invention, the input unit 304 is configured for receiving any kind of input (such as a button tap, a screen swipe, a text message, a selection of a section of a touchscreen) indicative of a message that the employee wishes to send to the patient. The notification device is configured to generate message data in response to the message input, and to transmit the input data to the monitoring apparatus via the central hub. The monitoring apparatus is configured for delivering the message to the patient based on the message data. For example, the employee may want to instruct the patient to keep calm and not to get up after a fall. If the input element includes a microphone, the employee may simply talk, and the audio message is passed to the patient. If the input element includes a screen, the screen may display a choice of messages, and enable the employee to select the desired message(s). The selection of the message creates the message data. The message data may correspond to audio data configured for being converted into an audio message by the monitoring unit.

In some embodiments of the present invention, the notification device 106 includes a user interface 306. The user interface may include a touchscreen and/or a button, and/or a keyboard for enabling the employee to caregiver to assume responsibility for a response to an alarm. Once the employee assumes responsibility for an alarm by interacting with the user interface, instruction data is generated and sent to the communication hub. The instruction data causes the communication hub to communicate with the notification devices of other employees and instructing these notification devices to stop the alarm, thus relieving others from responding. Optionally, the notification devices of the other employees convey the name or the employee who has assumed responsibility for the alarm. By stopping the alarm when it is no longer applicable to all employees except for the one who has assumed responsibility, the system of the present invention prevents unnecessary alarms, and therefore eliminates one of the sources of alarm fatigue.

The notification device may be a portable electronic device, laptop, tablet or other device that has a computer-readable medium having computer-executable instructions for performing the various functions of the patient monitoring program. Each portable electronic device may include a user interface for receiving instructions from a user (the user interface including, for example, a touch screen). The notification devices may also have software and/or hardware enabling communication between between a notification device and the central hub. Optionally, at least one of the notification devices is operable to communicate with one or more notification devices via one or more of infrared, mobile, or electromagnetic (e.g. BlueTooth) communication techniques.

Optionally, the notification device includes a processor and is configured for analyzing stored data and/or streaming data for patterns that may forecast activity and allow development or adjustment of plans. The data may to be processed by a set of algorithms to determine the current state of each patient and their respective alarm status. This allows for the combination of sensors to be utilized to determine if an action should be taken by the employees of a facility.

Figure 4:
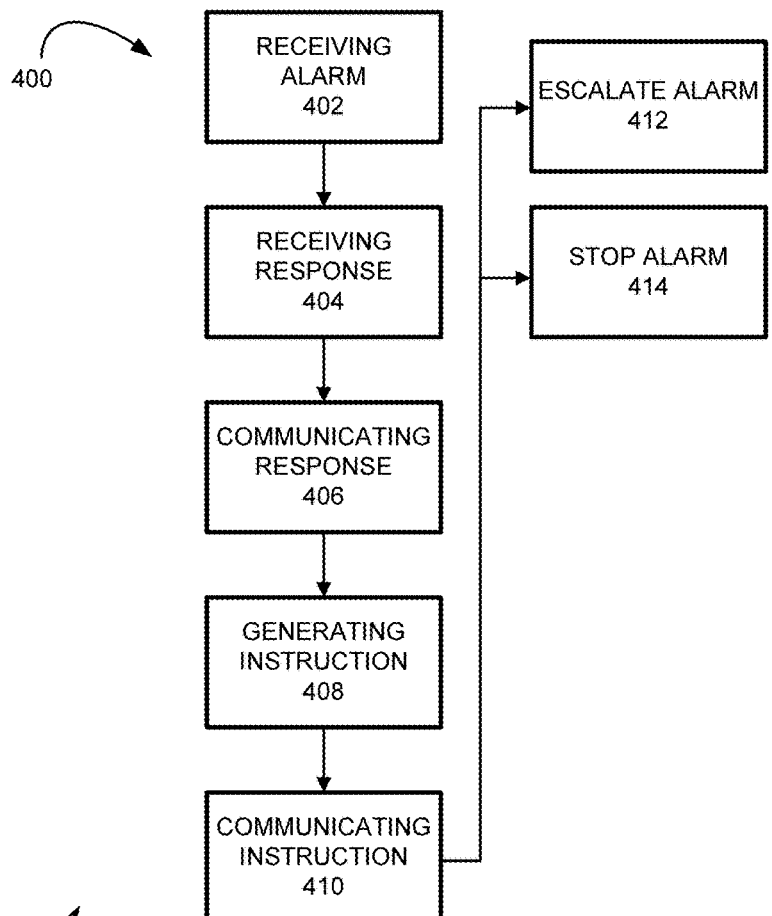
FIG. 4 is a flowchart illustrating a method of some embodiments of the present invention for notifying employees that an alarm has been responded to, following a response to the alarm by an employee.

FIG. 4 is a flowchart 400 illustrating a method for responding to an alarm based on a response by an employee.=. At 402, the notification devices of employees receive an alarm signal and inform the employees of the alarm. At 404, the notification device of one of the employees receives a response to the alarm by the respective employee. The response indicates that the employee assumes responsibility for the alarm. At 406, instruction data indicative of the response is communicated by the employee's notification device to the central hub. At 408, an instruction is generated by the central hub to notify employees of that the alarm is being taken care of. At 410, the instruction is sent to notification devices of other employees, and optionally also to the notification device of the employee who has assumed responsibility for the alarm. The alarm may be turned off by the employee when the employee demonstrates that he/she is at the source of the alert. This may be done by pushing a button on the monitoring apparatus that has generated the alarm, by touching the monitoring apparatus with the notification device, tracking indoor location of the employee to detect when the employee enters the room, etc.

At 412, if a certain time interval has passed and the employee has not yet checked the patient corresponding to the alarm, the alarm is escalated and the employees are notified that the alarm has not been dealt with. At 414, if proof of the employees presence by the patient has been received, the alarm is stopped, Reference is now made to FIGS. 5-9, which illustrates different configurations of the network formed by the monitoring apparatuses and the central communication hub. The discussed configurations include a mesh network and a star network. It should be noted that these configurations are non-limiting examples. Other network configurations (such as an ad-hoc configuration, a peer-to-peer configuration, and a tree configuration, for example) may also be used in the present invention. The scope of the present invention extends to any configuration of the network formed by the monitoring apparatuses and the central communication hub.

Figure 5:
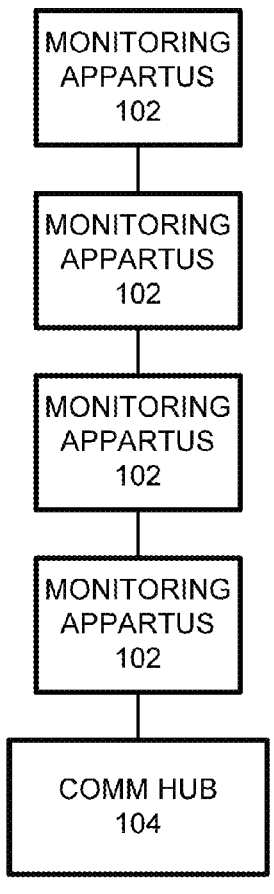
FIG. 5 is a block diagram illustrating a partial mesh configuration of a network of monitoring apparatuses, in which the monitoring apparatuses are connected in series, according to some embodiments of the present invention.

FIG. 5 is a block diagram illustrating a partial mesh configuration of a network of monitoring apparatuses, in which the monitoring apparatuses are connected in series, according to some embodiments of the present invention.

In the example of FIG. 5, the data transfer topology of the network is a variant of the partial mesh network topology/configuration. The monitoring apparatuses are disposed in series with each other. Any given monitoring apparatus is configured for receiving sensing data and/or an alarm signal from a preceding monitoring apparatus and for conveying the sensing data and/or first alarm signal to a following monitoring apparatus along with the sensing data and/or the alarm signal generated by the given monitoring apparatus. The last monitoring apparatus of the series is in direct communication with the central communication hub and is configured for conveying the sensing data and/or alarm signals of all other monitoring apparatuses along with the sensing data and/or the alarm signal generated by the last monitoring apparatus.

In this network configuration, each monitoring apparatus acts as a relay or booster to aid with the task of sending data along the network. The advantage of this configuration lies in the fact that a small infrastructure is needed to support and operate the network. Moreover, the infrastructure itself is formed as more monitoring apparatuses are added.

Figure 6:
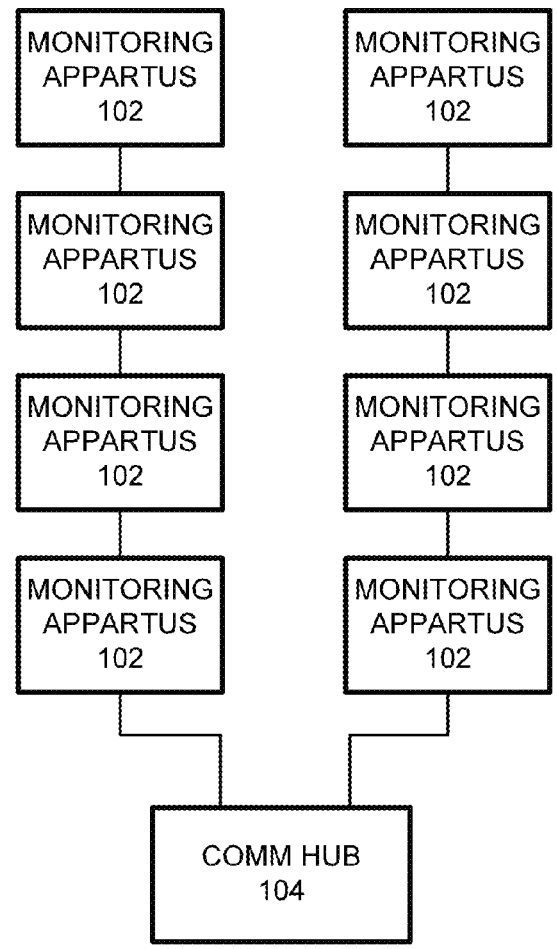
FIG. 6 is a block diagram illustrating a partial mesh configuration of a network of monitoring apparatuses, in which two sets of monitoring apparatuses connected in series are connected to the communication hub, according to some embodiments of the present invention.

FIG. 6 is a block diagram illustrating a partial mesh configuration of a network of monitoring apparatuses, in which two sets of monitoring apparatuses connected in series are connected to the communication hub, according to some embodiments of the present invention.

In the example of FIG. 6 two distinct sets of the monitoring apparatuses communicated with the central communication hub. In each set, the monitoring apparatuses are in series, as described in the example of FIG. 5. No communication between these is present. The advantage of the configuration of FIG. 6 lies in the fact that the length of each series is shortened. In this manner, the risk of data overload on a long series is diminished.

Figure 7:
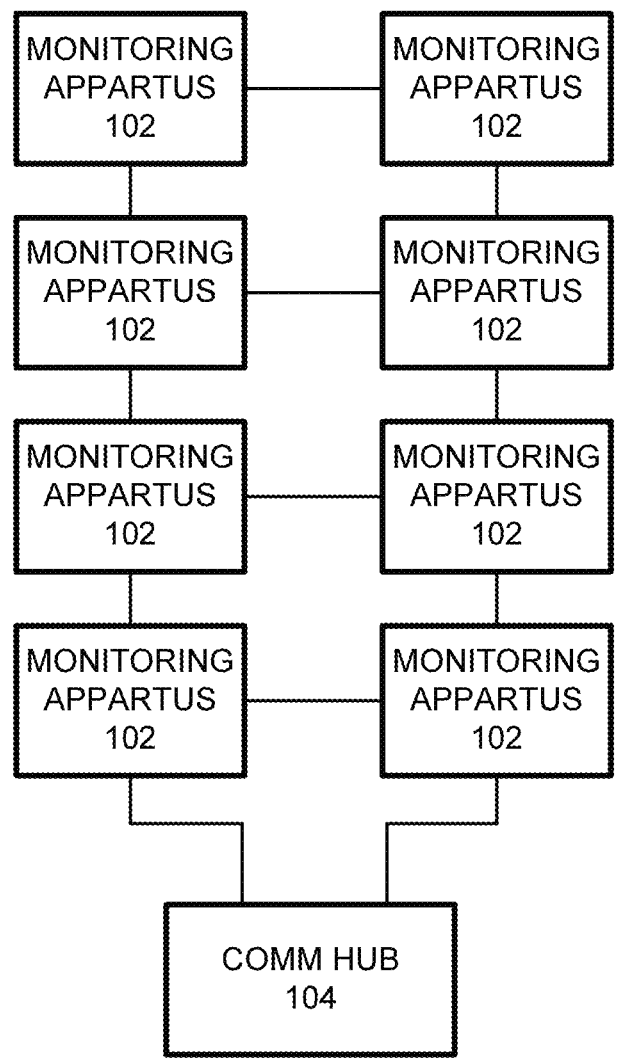
FIG. 7 is a block diagram illustrating a partial mesh configuration of a network of monitoring apparatuses, in which two sets of monitoring apparatuses connected in series are connected to the communication hub and monitoring apparatuses of one series are in communication with monitoring apparatuses of the other set, according to some embodiments of the present invention.

FIG. 7 is a block diagram illustrating a partial mesh configuration of a network of monitoring apparatuses, in which two sets of monitoring apparatuses connected in series are connected to the communication hub and monitoring apparatuses of one series are in communication with monitoring apparatuses of the other set, according to some embodiments of the present invention.

The example of FIG. 7 is similar to that of claim 6. However, in claim 6, each monitoring apparatus of a set is connected to at least one monitoring apparatus of the other set. This configuration enables the network to self-heal if a fault occurs along series.

Figure 8:
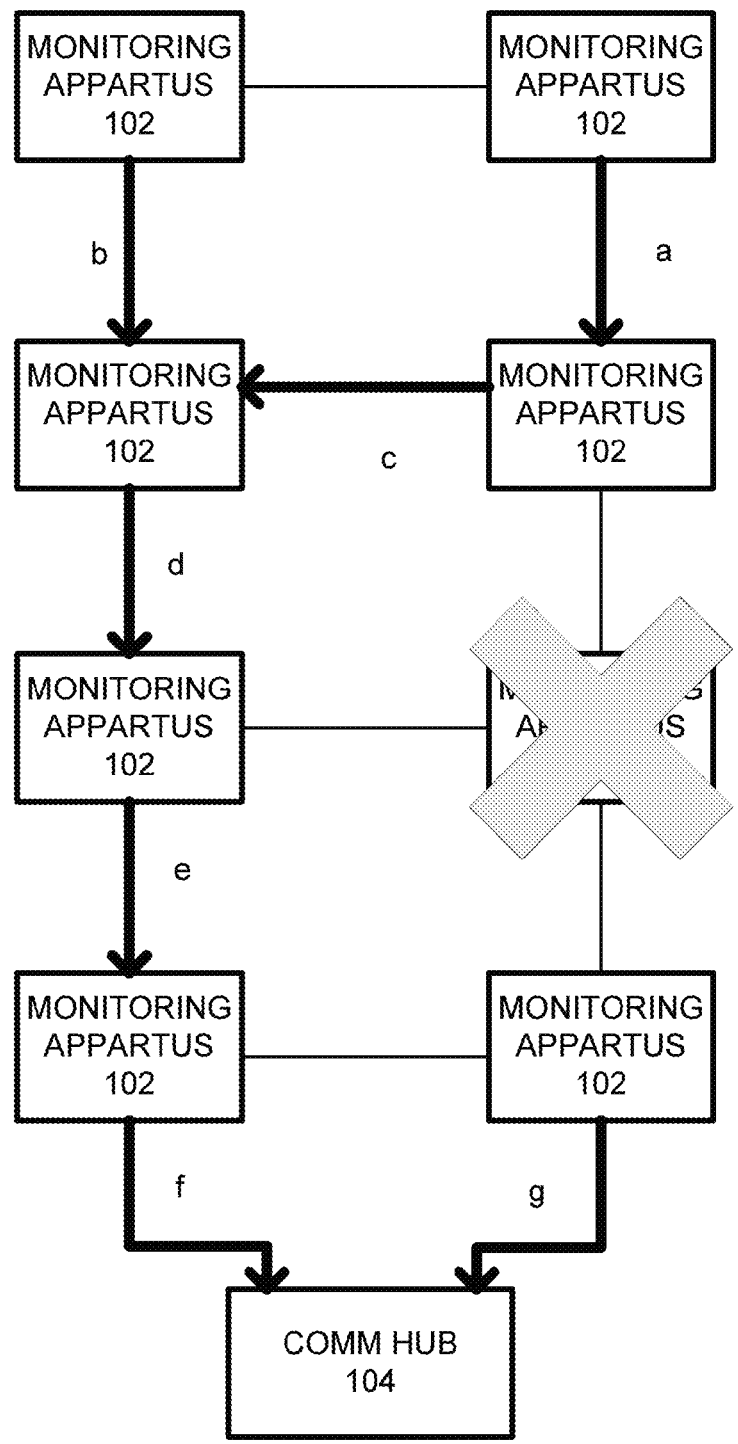
FIG. 8 is a block diagram illustrating an example of data flow in the configuration of claim 7.

The self-healing is shown in detail in FIG. 8, is a block diagram illustrating an example of data flow in the configuration of claim 7. In FIG. 8, the bold arrows illustrate the data flow.

In FIG. 8, any monitoring apparatus of the one set is configured for conveying data to the following monitoring apparatus in the same set. If the following monitoring apparatus in the same set is not responsive to communication, the monitoring apparatus is configured to convey the data to a monitoring apparatus of the other set, selected by the network's coordinator.

For example, in the left set of monitoring devices, all monitoring devices are responsive and functional. Therefore the data flows along the path composed by the segments b, d, e, and f. In the right set, the third monitoring device is not-responsive. Therefore, the second monitoring apparatus of the right set conveys data to a corresponding monitoring device of the left set. Thus data from the first and second monitoring apparatuses of the right set follows the path composed by segments a, c, d, e, and f. The last monitoring apparatus of the right set does not receive any data from the previous apparatus of the right set. This, however, does not prevent the last monitoring apparatus of the right set to convey the data generated therefrom to the communication hub via the segment g.

It can be seen that if a fault (e.g., failure of a monitoring apparatus) occurs, the coordinator (which may correspond to the communication hub or may be a separate element) detects the absence of data from the failed apparatus and directs the monitoring apparatus preceding the failed one in the path to sign on to a different monitoring apparatus assigned by the Coordinator. Thus, system integrity is maintained.

Figure 9:
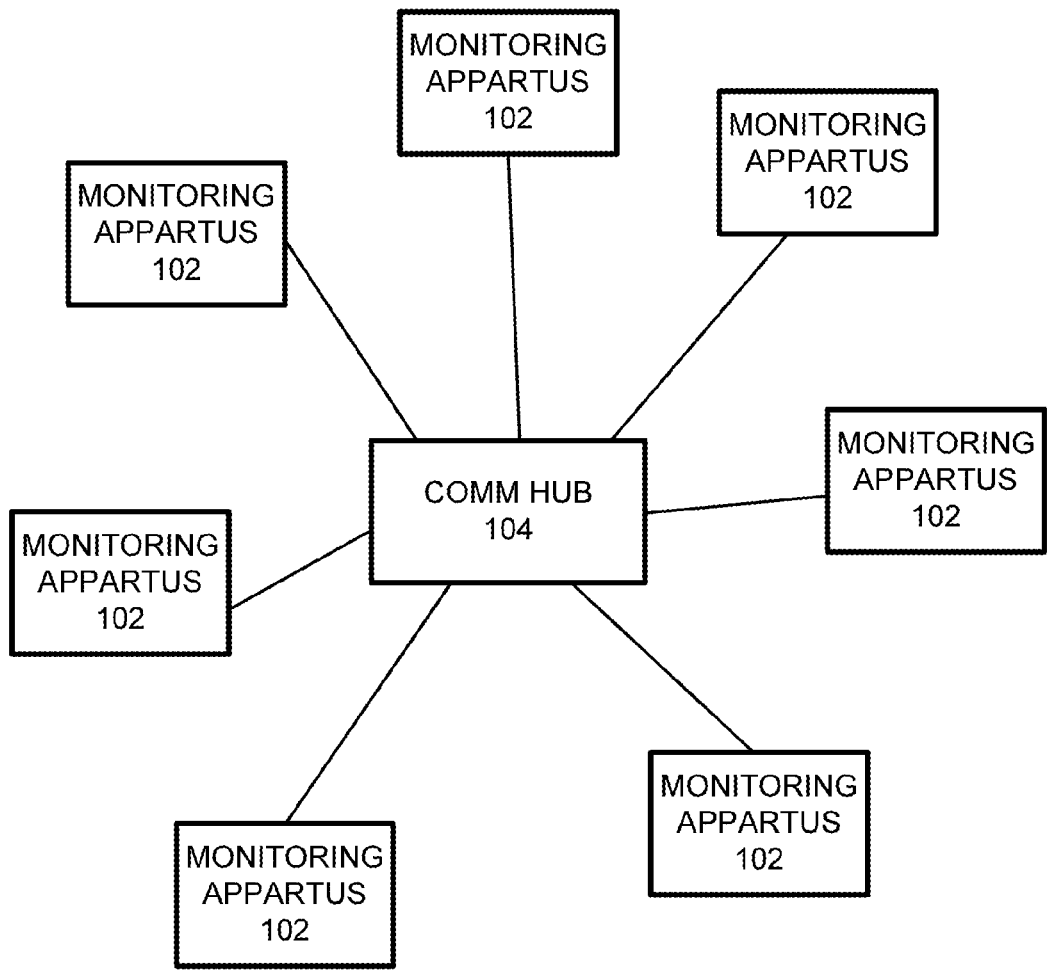
FIG. 9 is a block diagram illustrating a client-server network configuration of a plurality of monitoring apparatuses and the central communication hub, according to some embodiments of the present invention.

FIG. 9 is a block diagram illustrating a star network configuration of a plurality of monitoring apparatuses and the central communication hub, according to some embodiments of the present invention. In some embodiments of the present invention, each central apparatus is in direct connection with the central hub. Though this network configuration requires a large infrastructure, it is less sensitive to failures along the data path to the central hub.

Figure 10:
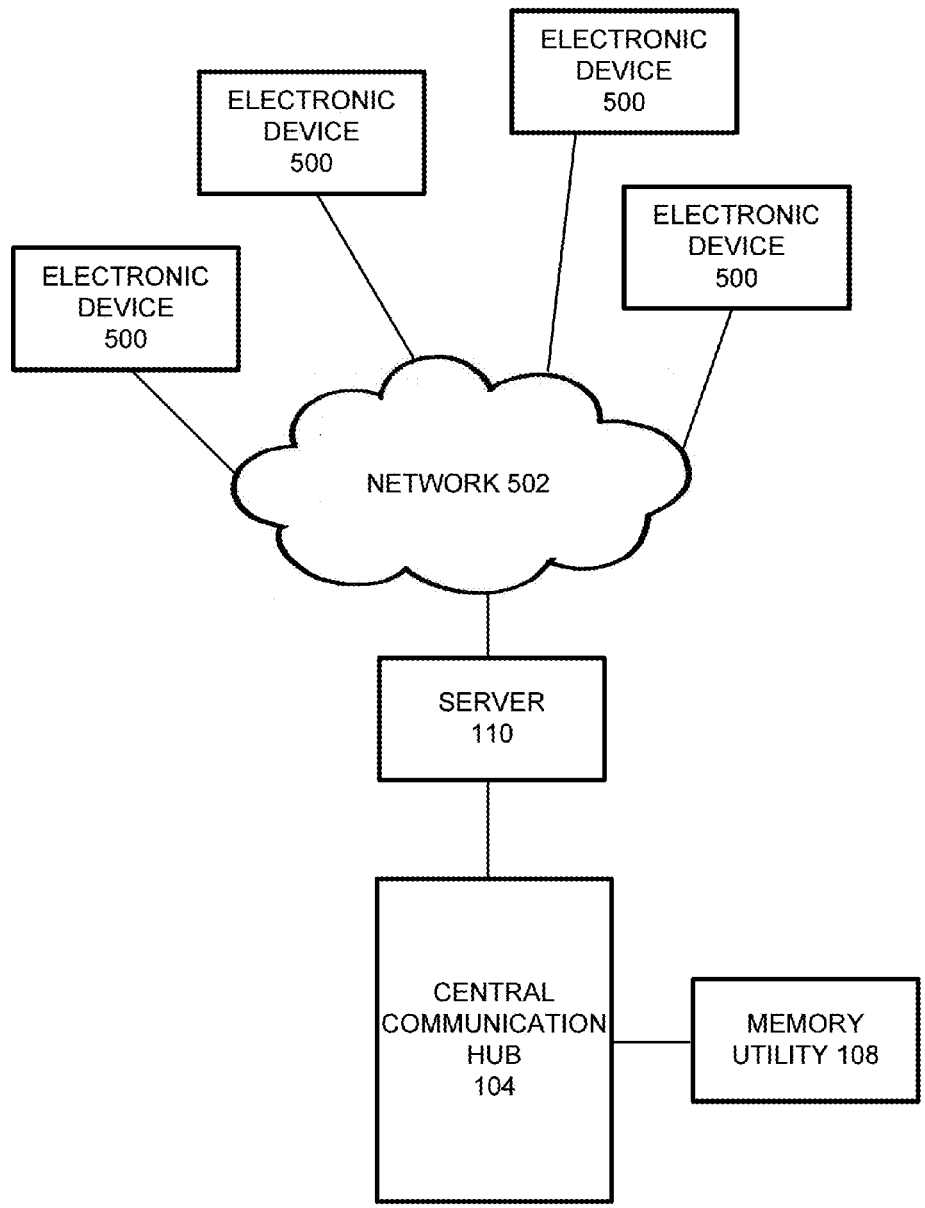
FIG. 10 is a block diagram illustrating a network which enables communication between the communication hub and one or more computing devices, according to some embodiments of the present invention.

FIG. 10 is a block diagram illustrating a network which enables communication between the communication hub and one or more computing devices, according to some embodiments of the present invention.

In the example of FIG. 10, the system of the present invention includes a server 110 and/or a memory utility 108 associated with the communication hub 104. In a variant, the server and memory utility are included in the communication hub.

The memory utility 108 is configured for storing the sensing data and/or alarm signals from each monitoring apparatuses in the care facility for a desired length of time (for example, at least three months). The central hub may include a transceiver that works across the network composed of the notification devices, allowing each notification device to reach the memory utility and download desired data therefrom.

In a variant, the server or communication hub periodically sends a signal to the monitoring apparatuses to transmit data stored in the monitoring apparatuses to the server or communication hub. If the transfer is successful, verified by software checks, then the monitoring apparatuses erase data stored therein. If, on the other hand, failure to collect data occurs, or if the memory units of the monitoring apparatuses has reached a stated percentage of its storage capacity (for example, 80%), the central hub sends a signal to the notification devices to notify that the memory is nearly full. At that point the data can be collected from the central hub or from the individual control boxes using a USB device or over a repaired network.

In some embodiments of the present invention, the server 110 can be accessed by a plurality of computing devices 500 via a network 502. In this manner, the monitoring apparatuses can be reprogrammed via the server or via the computing devices 500.

Optionally, the communication hub 104 is configured for generating reports relating to one or more patients, based on the data received from the monitoring apparatus(es) associated with the one or more patients. The reports may be stored in the memory utility 108 and/or in the server 110. These reports may be remotely accessible by family members of the patients via communication of the electronic devices 500 with the server 110 via the network 502. Optionally, the network 502 includes the Internet. Optionally, the reports are password protected, to safeguard the privacy of the patients.

In a variant, the central server is the repository for data collected by periodically sending a signal to the control boxes or central hub to transmit stored data. If the transfer is successful, verified by software checks, then the control box or central hub erases its data and starts over. If, on the other hand, the network fails to collect data or if the control box has reached a stated percentage of its storage capacity (for example, 80%), the central hub sends a signal to the notification devices that its memory is nearly full. At that point the data could be collected from the central hub or from the individual control boxes using a USB device or over a repaired network.

Optionally or additionally, the notification device has sufficient memory to store data for each patient in the care facility for a desired length of time (for example, at least three months). After a certain time interval (e.g. one month) that is less than or equal to the desired length of time, the data may be downloaded onto a universal serial bus (USB) drive or hard disk. The previous months' data will remain on the notification device so that caregivers can compare a patient's current behavior to the previous months and develop care plans for each patient.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for monitoring multiple patients within a facility, the system comprising:
   (a) a plurality of monitoring apparatuses, each monitoring apparatus corresponding to at least one respective patient, each monitoring apparatus being configured for being in communication with a respective sensing unit which comprises at least one sensor configured for creating sensing data indicative of a status of the patient, and each monitoring apparatus comprising:
      (a1) a respective control unit configured for being in wired and/or wireless communication with the sensing unit, and for receiving the sensing data; and (a2) a respective communication unit, configured for receiving the sensing data from the control unit and transmitting the sensing data to a remote location;

(b) a central communication hub configured for being in communication with the plurality of monitoring apparatuses, and for receiving the sensing data from each communication unit, wherein the central communication hub and/or the control unit is configured for processing the sensing data, and generating an alarm signal if at least a portion of the sensing data deviates from a predetermined pattern, the deviation being indicative of an undesirability in the patient's status;

(c) a plurality of notification devices configured for being in wired and/or wireless communication with the central communication hub, each notification device being accessible to one or more employees of the facility, and each notification device comprising a communication element configured for receiving the alarm signal and an output element informing the one or more employee about the source of the alarm signal, wherein each of at least some of the notification devices comprise a respective user inter face configured for enabling the one or more employees to respond to the alarm, the response causing the respective device to generate instruction data and send the instruction data to the central communication hub, the instruction data causing the central communication hub to communicate with all other notification devices in use so as to inform the other employees that the alarm has been responded to.

2. The system of claim 1, wherein the patient's status comprises at least one of: the patient's presence in at least one particular location, absence from at least one particular location, a position of the patient, a stance of the patient.

3. The system of claim 1, wherein the central hub is associated with a memory utility configured for storing the sensing data and/or the alarm signal corresponding to each monitoring apparatus.

4. The system of claim 3, wherein the central hub is configured for monitoring an amount of free memory in the memory utility, and for generating and sending a notification to at least one of the notification devices when the amount of free memory is less than a predetermined amount.

5. The system of claim 3, wherein at least one of the notification devices is configured for storing the sensing data and/or the alarm signal when the amount of free memory in the memory utility is less than a predetermined amount.

6. The system of claim 1, wherein each monitoring apparatus comprises at least one output unit configured for delivering a message to the respective patient, when the alarm is generated.

7. The system of claim 6, wherein the output unit is associated with a memory unit storing a plurality of messages corresponding to a plurality of causes due to which the alarm has been generated, the output unit being configured for selecting one of the messages, depending on the cause for due to which the alarm has been generated.

8. The system of claim 6, wherein:
the central communication hub is configured for generating data indicative of the message in response to the alarm signal, and for transmitting the data indicative of the message to the monitoring apparatus; and
the output unit is configured for delivering the message based on the data indicative of the message.

9. The system of claim 1, wherein:
at least one of the monitoring apparatuses comprises at least one output unit;

at least one of the notification devices comprises at least one input unit configured for receiving a message input from the one or more employees, the message input being indicative of a message to the patient;
the central communication hub is configured for delivering the message input to the at least one monitoring apparatus;
the at least one output unit is configured for delivering a message to the corresponding patient, the message being based on the message input.

10. The system of claim 9, wherein the message input comprises at least one of: a press of a button of the notification device, a tap of a button of the notification device, a touch of a touchscreen of the notification device, a swipe of the touchscreen of the notification device.

11. The system of claim 1, wherein the notification device is configured for emitting a low-volume warning sound in response to receiving the alarm signal.

12. The system of claim 1, wherein the notification device comprises a display configured for displaying an image indicative of the source of the alarm signal in response to the notification device's receipt of the alarm signal.

13. The system of claim 12, wherein the image comprises a map of the facility and a mark on the map displaying a location of the source of the alarm.

14. The system of claim 1, wherein the notification device is configured for generating haptic feedback in response to receiving the alarm signal.

15. The system of claim 1, wherein at least one control unit is connected to a plurality of sensing units associated with a plurality of respective patients.

16. The system of claim 1, wherein the control unit is configured for being in communication with at least one sensing unit which comprises a plurality of sensors.

17. The system of claim 16, wherein each sensor is connected to the control unit and is configured for communicating with the control unit by wire and/or wirelessly.

18. The system of claim 1, wherein:
the monitoring apparatuses are disposed in series with each other in a partial mesh network configuration, such that any given monitoring apparatus is configured for receiving first sensing data and/or a first alarm signal from a preceding monitoring apparatus and for conveying the first sensing data and/or the first alarm signal to a following monitoring apparatus along with the sensing data and/or the alarm signal generated by the given monitoring apparatus; and
a last monitoring apparatus of the series is configured to be in direct communication with the central communication hub and for conveying to the central communication hub the sensing data and/or alarm signals of all other monitoring apparatus along with the sensing data and/or the alarm signal generated by the last monitoring apparatus.

19. The system of claim 18, wherein the monitoring apparatuses comprises:
a first set of monitoring apparatuses disposed in a first series, such that a last monitoring apparatus of the first series is configured to be in direct communication with the central communication hub; and
a second set of monitoring apparatuses disposed in a second series, such that a last monitoring apparatus of the second series is configured to be in direct communication with the central communication hub.

20. The system of claim 19, wherein:
any particular monitoring apparatus of the first set is configured to be in communication with a previous communication apparatus, a following apparatus in the first set, and at least one monitoring apparatus of the second set;

any monitoring apparatus of the first set is configured for conveying the received and generated sensing data and/or alarm signal to the following monitoring apparatus of the first set;

if the following monitoring apparatus in the first set is not responsive to communication, the monitoring apparatus of the first set is configured to convey the received and generated sensing data and/or alarm signal to the at least one monitoring apparatus of the second set;

any particular monitoring apparatus of the second series is configured to be in communication with a previous monitoring apparatus, a following monitoring apparatus in the second set, and at least one monitoring apparatus of the first set;

any monitoring apparatus of the second set is configured for conveying the received and generated sensing data and/or alarm signal to the following monitoring apparatus of the second set;

if the following monitoring apparatus in the second set is not responsive to communication, the monitoring apparatus of the second set is configured to convey the received and generated sensing data and/or alarm signal to the at least one monitoring apparatus of the first set.

21. The system of claim 1, wherein the central communication hub is associated with a server, and at least one of the monitoring apparatuses is configured for being programmable via the server and/or via a computing device in communication with the server.

22. The system of claim 1, wherein:
the central communication hub is associated with a server;
the central communication hub is configured for using the sensing data corresponding to at least one of the patients for generating a report relating to the at least one of the patients;
wherein the report is accessible via the server and/or via a computing device in communication with the server.

23. The system of claim 1, wherein each notification device is configured for being carried by a respective employee.

24. The system of claim 1, wherein at least one of the monitoring apparatuses comprises a respective sensing unit.

* * * * *